United States Patent [19]
Wanzenböck

[11] Patent Number: 6,126,085
[45] Date of Patent: Oct. 3, 2000

[54] FRAGRANCE DISPENSER

[75] Inventor: Karl Wanzenböck, Leobersdorf, Austria

[73] Assignee: Fildan Accessories Corporation, Englewood, N.J.

[21] Appl. No.: 09/363,056

[22] Filed: Jul. 29, 1999

[51] Int. Cl.[7] .................................................. A61L 9/04
[52] U.S. Cl. ................... 239/36; 239/53; 239/57
[58] Field of Search .................. 239/36, 53, 54, 239/55, 56, 57; 63/DIG. 2, 1.14, 1.15, 1.18; 2/56, 55, 54, 53, 171.2; 450/89, 37, 38, 150; 24/3.1, 3.12, 3.7, 5, 6, 3.3, 3.6; 40/1.5; 248/314, 316.2, 316.7

[56] References Cited

U.S. PATENT DOCUMENTS

| | | |
|---|---|---|
| 168,972 | 10/1875 | Dayton . |
| 2,109,092 | 2/1938 | Roll . |
| 3,784,102 | 1/1974 | Stults . |
| 3,823,873 | 7/1974 | Miller, Jr. et al. . |
| 4,451,258 | 5/1984 | Jensen . |
| 5,196,171 | 3/1993 | Peltier . |
| 5,240,699 | 8/1993 | Osada et al. . |
| 5,989,101 | 11/1999 | Jenn-Shyang et al. . |

*Primary Examiner*—Andres Kashnikow
*Assistant Examiner*—Christopher S. Kim
*Attorney, Agent, or Firm*—Herbert Dubno

[57] ABSTRACT

A fragrance dispenser for a brassiere has a holder molded from plastic and connected to the brassiere. The holder is of droplet shape and has a pocket from which a neck extends, the pocket receiving a sintered metal or mineral porous disk impregnated with perfume and held in the pocket by a deflectable tongue on the neck.

18 Claims, 3 Drawing Sheets

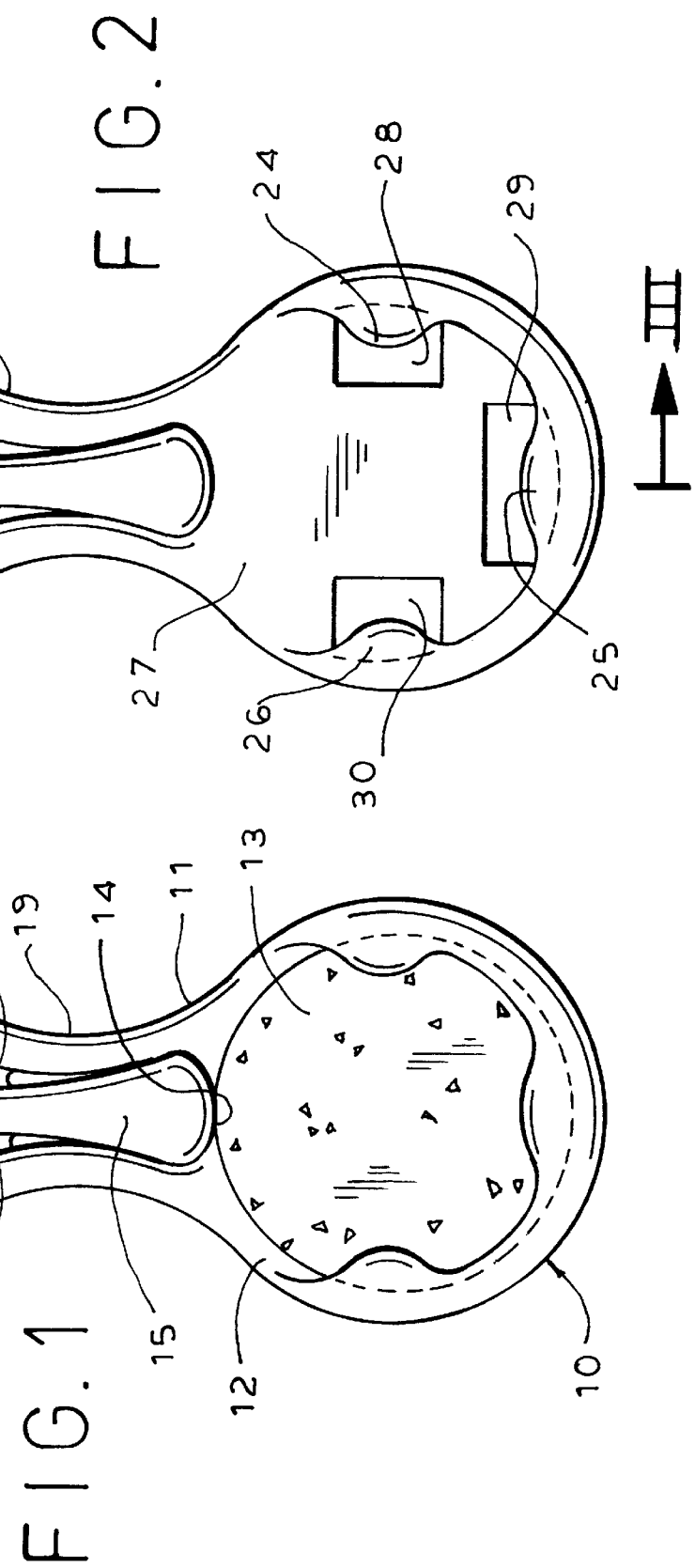

FRAGRANCE DISPENSER

FIELD OF THE INVENTION

My present invention relates to a fragrance dispenser for attachment to an undergarment or brassiere and, more particularly, to a fragrance dispenser having esthetic character and capable of attachment to a brassiere with the capacity to release a variety of aromas.

BACKGROUND OF THE INVENTION

While it is not uncommon for an individual to apply a dab of perfume to a portion of the anatomy which is covered by clothing and dispensers for fragrances have been provided heretofore which can be worn by an individual, a basic problem with such devices is that the particular fragrance which is dispensed is usually fixed at manufacture. In some cases, moreover, the device may be unesthetic and hence should be concealed beneath a garment.

OBJECTS OF THE INVENTION

It is the principal object of the present invention to provide a fragrance dispenser which is free from the drawbacks of such earlier devices.

Another object of this invention is to provide a fragrance dispenser which is capable of dispensing a variety of fragrances and in which the fragrance can be altered from time to time.

Still another object of the invention is to provide an esthetic fragrance dispenser which has a long useful life and, in particular, can be used with an undergarment or brassiere.

SUMMARY OF THE INVENTION

These objects and others which will become apparent hereinafter are attained, in accordance with the invention in a dispenser for a fragrance which comprises a droplet-shaped holder having a narrow upper portion, a wide lower portion forming an upwardly open pocket, a disk of a porous material contained in the pocket and impregnated with a volatile liquid producing a fragrance upon evaporation, and means at the upper end of the holder enabling attachment of the holder to an undergarment or brassiere.

According to a feature of the invention, the neck of the holder comprises a deflectable member which blocks withdrawal of the disk from the pocket until that member is intentionally deflected, thereby preventing unintentional loss of the disk.

According to a feature of the invention, the disk is formed from sintered metal particles which may be, for example, spherical particles of brass, thereby having a gold finish. The holder itself may be composed of a synthetic resin material, for example an acrylonitrile-butadiene-styrene terpolymer (ABS) and provided with a metallic, preferably gold, finish or coating.

The disk may be a flat disk and, as an alternative to a sintered metal disk, may be composed of any porous mineral matter, preferably one which has biological compatibility with the body, for example, a natural pumice or lava stone.

According to the invention, the disk is impregnated with a few drops of perfume of the user's selection, i.e. a favorite perfume, and can dispense the fragrance of that perfume over an extended period of time.

The means for attaching the holder to the brassiere may be eyelets in the upper end of the holder through which loops can affix the holder to the brassiere releasably or through which the holder can be stitched to the brassiere. The disk can be removed for laundering of the garment to which the holder is attached and the holder will not impede laundering.

The porous disk itself may be washed and rinsed to eliminate traces of a previously used perfume when the user wishes to alter the dispensed scent. Of course the disk can be of any desired color and the color of the disk and/or of the holder can be matched to the color of the fabric of the brassiere.

The holder may be marketed in a kit with ampoules, vials or bottles of a particular perfume or of a number of different scents, whereby the disks may be packaged, following impregnation with a scent, in an envelope impermeable to the vapors of the perfume, and the holder can be sold with a number of different disks with different finishes, colors and impregnating perfumes as may be desired to enable a rapid changeover from one scent to another.

BRIEF DESCRIPTION OF THE DRAWING

The above and other objects, features, and advantages will become more readily apparent from the following description, reference being made to the accompanying drawing in which:

FIG. 1 is an elevational view of a fragrance dispenser according to the invention;

FIG. 2 is an elevational view of the dispenser of FIG. 1 with the fragrance stone removed, i.e. showing only the holder;

SPECIFIC DESCRIPTION

Figure 6:
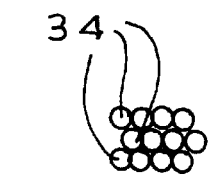
FIG. 6 is an enlarged detail of a portion of a fragrance stone.
Figure 3:
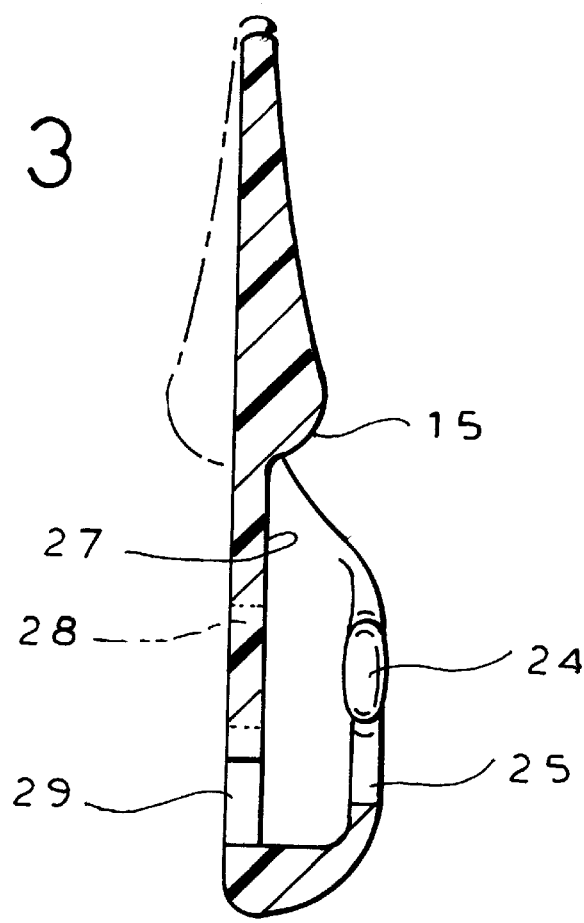
FIG. 3 is a sectional view along the line III—III of FIG. 2.

As can be seen from FIG. 1, the fragrance dispenser 10 of the invention comprises a holder 11 molded in one piece from a synthetic ring, e.g. an ABS, and coated with a metallic coating, preferably in a gold finish. In a pocket 12 of this holder a fragrance stone 13 is removably received and is held in place by an end 14 of a tongue 15 which is deflectable into the plane of the wrapper of FIG. 1. The tongue 15 is connected at a ligature 16 to a pair of inwardly extending bights 17 and 18 and the upper end of a neck 19 of the holder.

Figure 7:
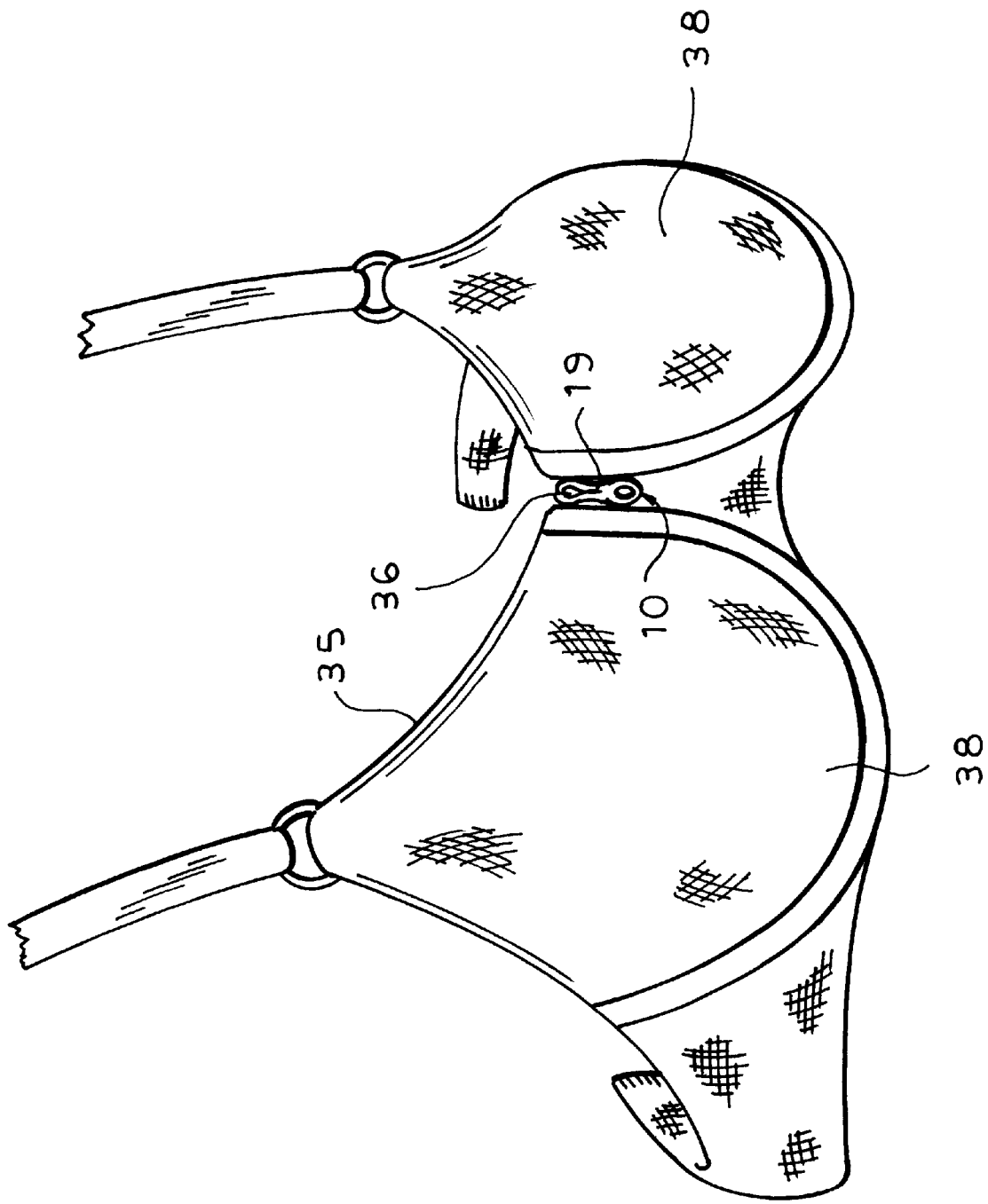
FIG. 7 is a perspective view showing a brassiere provided with the fragrance dispenser.

The bights 17 and 18 define eyelets or openings 20 and 21 through which stitching can pass to hold the dispenser onto a brassiere (FIG. 7). A pair of stabilizing webs 22 and 23 are provided at the neck between the bights 17 and 18 and the ligature 16.

Figure 4:
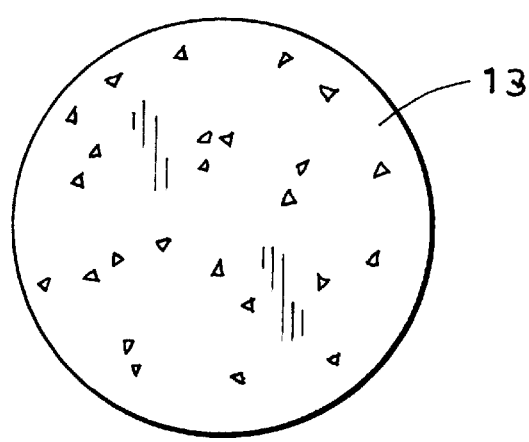
FIG. 4 is an elevational view of the fragrance stone.
Figure 5:
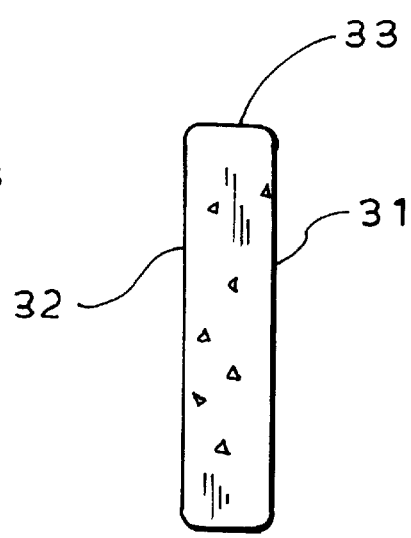
FIG. 5 is a side elevational view thereof

As will be apparent from FIG. 2, the pocket 12 can be formed by a plurality of inwardly extending projections 24, 25, 26 overhanging the back 27 of the pocket which is provided with openings 28, 29 and 30 facilitating the releases of scent from the fragrance stone 13. As can be seen from FIGS. 4 and 5, the fragrance stone 13 can be a circular disk of a diameter fitting into the pocket 12 and so that it is overhung by the projections 24–26. The circular disk has flat sides 31 and 32 and a cylindrical periphery 33. It may be composed of a biocapillary material, for example, lava stone or, as shown in FIG. 6, may be sintered from spherical metal beads 34 to leave capillaries and interstices in which the perfume can be stored.

In practice, the cylindrical disk 13 can be anointed with a few drops of perfume, and pressed into the pocket passed the tongue 15 which can be deflected into the position shown in dot-dash lines and which can then hold the stone in place.

Where the fragrance dispenser is attached to an undergarment such as a brassiere, it will dispense its aroma as long as the brassiere is worn and can be refreshed with perfume at any time. The stones may be interchangeable with one another and replaceable if a scent is to be charged and the stones can be washed and dried to prepare them to receive other perfumes.

In FIG. 7, stitching 36 attaches the fragrance dispenser to a brassiere 35 at the web 37 connecting the two cups 38 thereof. The fragrance dispenser can be mounted on a fitting of the brassiere, e.g. a slider or ring of the strap system, a front connector for a front opening brassiere, or any fabric portion thereof.

I claim:

1. A fragrance dispenser for an undergarment, comprising:
   a holder formed with a pocket, a neck and means at an upper end of said neck for securing said holder to an undergarment; and
   a porous disk impregnated with perfume and received in said pocket, said neck being formed with a deflectable tongue releasably retaining said disk in said pocket.

2. The fragrance dispenser as defined in claim 1 wherein said pocket is formed by a plurality of inwardly extending projections.

3. The fragrance dispenser as defined in claim 2 wherein said holder is provided with a back supporting said disk and provided with a plurality of openings.

4. The fragrance dispenser as defined in claim 3 where said disk is composed of sintered metal particles.

5. The fragrance dispenser as defined in claim 4 wherein said disk is composed of sintered generally spherical brass particles.

6. The fragrance dispenser as defined in claim 4 wherein said disk is composed of a porous mineral composition.

7. The fragrance dispenser as defined in claim 6 wherein said disk is composed of porous stone.

8. The fragrance dispenser as defined in claim 4 wherein said holder is molded in one piece from a plastic.

9. The fragrance dispenser as defined in claim 8 wherein said holder is molded from acrylonitrile-butadiene-styrene terpolymer and has a metallic finish.

10. The fragrance dispenser as defined in claim 9 wherein said holder has droplet shape and said tongue is connected to a pair of inwardly extending bights defining respective eyelets.

11. A brassiere having a pair of cups and a fragrance dispenser connected to said brassiere, said fragrance dispenser comprising a droplet shaped holder formed with a holder formed with a pocket, a neck and means at an upper end of said neck for securing said holder to an undergarment; and
    a porous disk impregnated with perfume in said pocket, said neck being formed with a deflectable tongue releasably retaining said disk in said pocket.

12. A brassiere having a pair of cups and a fragrance dispenser connected to said brassiere, said fragrance dispenser comprising a droplet shaped holder formed with a holder formed with a pocket, a neck and means at an upper end of said neck for securing said holder to an undergarment; and
    a porous disk impregnated with perfume in said pocket, said pocket being formed by a plurality of inwardly extending projections.

13. A brassiere as defined in claim 12 wherein said holder is provided with a back supporting said disk and provided with a plurality of openings.

14. A brassiere as defined in claim 12 where said disk is composed of sintered metal particles.

15. A brassiere as defined in claim 12 wherein said disk is composed of sintered generally spherical brass particles.

16. A brassiere as defined in claim 12 wherein said disk is composed of a porous mineral composition.

17. A brassiere as defined in claim 12 wherein said disk is composed of porous stone.

18. A brassiere as defined in claim 12 wherein said holder is molded in one piece from a plastic.

\* \* \* \* \*